(12) United States Patent
Inzer

(10) Patent No.: US 9,011,305 B2
(45) Date of Patent: Apr. 21, 2015

(54) GRIPPER WRAPS

(76) Inventor: John Inzer, Longview, TX (US)

(*) Notice: Subject to any disclaimer, the term of this patent is extended or adjusted under 35 U.S.C. 154(b) by 472 days.

(21) Appl. No.: 13/338,958

(22) Filed: Dec. 28, 2011

(65) Prior Publication Data

US 2013/0172156 A1    Jul. 4, 2013

(51) Int. Cl.
*A63B 71/12* (2006.01)
*A63B 21/072* (2006.01)
*A63B 23/04* (2006.01)

(52) U.S. Cl.
CPC ......... *A63B 71/1225* (2013.01); *A63B 21/0724* (2013.01); *A63B 2023/0411* (2013.01); *A63B 2071/125* (2013.01); *A63B 2209/00* (2013.01)

(58) Field of Classification Search
USPC ........ 482/137, 139, 148, 92; 602/75; 428/220
See application file for complete search history.

(56) References Cited

U.S. PATENT DOCUMENTS

| | | | | |
|---|---|---|---|---|
| 4,984,566 A * | 1/1991 | Sekine et al. | ...................... | 602/6 |
| 5,407,421 A * | 4/1995 | Goldsmith | ......................... | 602/5 |
| 5,501,679 A * | 3/1996 | Krueger et al. | ............... | 604/393 |
| 5,691,034 A * | 11/1997 | Krueger et al. | ............... | 428/152 |
| 5,887,277 A * | 3/1999 | Lohman | .............................. | 2/16 |
| 6,048,326 A * | 4/2000 | Davis et al. | ...................... | 602/26 |
| 6,402,712 B1 * | 6/2002 | Gauvry | ............................ | 602/26 |
| 7,937,852 B1 * | 5/2011 | Krehbiel | .......................... | 36/2 R |
| 8,556,841 B2 * | 10/2013 | Daneshvar | ........................ | 602/75 |
| 2004/0098841 A1 * | 5/2004 | Crosby et al. | .................. | 24/16 R |
| 2005/0107725 A1 * | 5/2005 | Wild et al. | ..................... | 601/152 |
| 2007/0022519 A1 * | 2/2007 | South | ................................. | 2/239 |
| 2012/0059302 A9 * | 3/2012 | Hou | ................................. | 602/75 |
| 2012/0066809 A1 * | 3/2012 | Goth et al. | .......................... | 2/16 |

* cited by examiner

*Primary Examiner* — Stephen Crow
(74) *Attorney, Agent, or Firm* — Dinsmore & Shohl LLP

(57) ABSTRACT

Embodiments of the current invention are directed towards solving the need for weightlifting wraps which prevent slippage, increase rebound potential, allow simpler application, and provide greater stability. An embodiment of the invention comprises: gripper wraps made of stretchable material; the gripper wraps having exposed rubber strands on one outer surface of the gripper wraps; the exposed rubber strands arranged in an offset lattice configuration, wherein the exposed rubber strands have a coefficient of friction sufficient to grip the previous layer of wrap.

15 Claims, 7 Drawing Sheets

GRIPPER WRAPS

BACKGROUND

Weightlifters wear supportive weightlifting wraps for two primary reasons: to protect and provide stability to the joints; and to provide kinetic energy during joint flexion (thereby increasing the amount of weight they can lift in exercises that require bending of the joints). Examples of exercises that require joint bending may include: squats; dead lifts; lunges; leg extensions; leg presses; dumbbell bench press; triceps kick backs; and bicep curls.

An example of the use of weightlifting wraps for support includes the use of weightlifting wraps around the knees. In weightlifting exercises requiring knee bending, the heavy weights used exert tremendous point load pressure on the knee joints. Knee wraps hold the knee joint in place. As the knee moves into flexion, the knee wraps are compressed, thereby storing potential energy. As the knee is extended, and the angle of knee flexion decreases, the wraps "rebound" and return the potential absorbed in compression into kinetic energy. The rebound provides an increase in the amount of weight the lifter can lift.

Weightlifting wraps are typically constructed from flexible or elastic material that rebounds from being stretched. The weightlifter puts the wraps on by stretching and rolling each wrap tightly around the joint. After the full length of the wrap is wrapped on the joint, the end of the wrap is tucked into one of the layers of wrapped material. The weightlifting wraps provide support to athletes' joints. However, several problems exist concerning safety, effectiveness, and ease of use.

One problem of weightlifting wraps exists due to slippage of the individual layers of wrapped material. Each revolution of wrap lies down against wrap material of the revolution before it. A lack of friction between each layer causes the wrap to from the other layers during joint flexion. The slippage limits the amount of support the weightlifting wrap can provide the lifter. Sudden or intermittent slippage can cause loss of stability and cause injury to the weightlifter.

Weightlifters have attempted to address the problem of slippage by applying either "gym chalk" (magnesium carbonate) or "sticky-spray" (sticky solution in aerosol spray cans). The gym chalk or sticky spray helps the wrap layers to hold, or grip, to each other. Gym chalk may leave residue on the floor and clothing. In addition, gym chalk only provides a small amount of friction between the layers but does not stop the slipping. Sticky spray is difficult to clean off the skin and wrap material, toxic to breathe, attracts dirt, and rubs off on clothing. Both gym chalk and sticky spray are expensive, clutters a weightlifter's gym bag, and occupies space. Gym chalk and sticky spray require time to buy, apply, store, and organize.

Another problem presented by weightlifting wraps concerns limited rebound potential. Conventional weightlifting wraps are constructed of a yarn or cloth material and may sometimes include an elastic material on the inside of such wrap. In the example involving knee wraps, the yarn or cloth material making direct contact with the back of the knee provides inferior rebound, compared to the effects of having a rubber tennis ball behind the knee, for example. To get similar rebound from the use of yarn or cloth material would require densely wound wraps. Wrapping such wraps in a densely wound configuration presents several problems including: the requirement of a "modulus" (power required to pull the wrap tight) greater than a single lifter could pull with the arms; would squeeze the joints so severely that it would be too painful to keep the wrap on the joints; and would dramatically reduce circulation.

Another problem presented by such weightlifting wraps includes the difficulty of application. It is desirable to wrap the weightlifting wraps tightly to increase support, protection, and performance. During the wrapping of the joints, the hands of the lifter or the lifter's handler can lose grip on the wraps. Such knee wraps uncoil almost completely unless the wraps are kept in control by the hands or by tucking the end of the wraps inside a layer of wrap. The wrapping process must then be repeated. This repetitive process results in lost time, and lost mental and physical energy. Competitive lifters are given a certain amount of time (usually one to three minutes) to get on the platform and perform the exercise after the lifter's name is called. When a wrap uncoils before or during this time, the lifter faces a dilemma: lifting with an uncoiled wrap; or risking disqualification by attempting to re-wrap in time.

Another problem arises due to the instability of weightlifting wraps. Such weightlifting wraps may shift position during an exercise. This shift in position causes instability in the weightlifter and "jitteriness." This causes the lifter's muscles to work hard to compensate for the "jittery" motion. The extra work of the muscles reduces the lifter's overall performance and decreases the amount of weight the lifter can lift. This extra muscle work also requires more mental and physical energy output, resulting in loss of endurance during a tournament or workout. The instability also significantly reduces the protective benefit from weightlifting wraps. Therefore, a need arises for weightlifting wraps which prevent slippage, increase rebound potential, allow simpler application, and provide greater stability.

SUMMARY

Embodiments of the current invention are directed towards solving the need for weightlifting wraps which prevent slippage, increase rebound potential, allow simpler application, and provide greater stability. An embodiment of the invention comprises: gripper wraps made of stretchable material; the gripper wraps having exposed rubber strands on one outer surface of the gripper wraps; the exposed rubber strands arranged in an offset lattice configuration, wherein the exposed rubber strands have a coefficient of friction sufficient to grip the previous layer of wrap.

It is an object of the current invention to provide gripper wraps which prevent sliding and slipping of the individual layers of wraps.

It is another object of the current invention to provide gripper wraps which provide rebound through the use of exposed rubber strands on one or both of the outer surfaces of the weightlifting gripper wraps.

It is another object of the invention to provide gripper wraps which allow ease of application and incorporate the use of exposed rubber strands on one or both of the outer surfaces of the weightlifting gripper wraps to decrease the modulus during application.

It is another object of the invention to provide gripper wraps to incorporate exposed rubber strands on one or both of the outer surfaces of the weightlifting gripper wraps which are woven into the fabric, and may be configured in an offset lattice configuration.

It is further an object of the invention to provide weightlifting gripper wraps to incorporate exposed rubber strands on one or both of the outer surfaces of the weightlifting gripper wraps wherein the exposed rubber strands have a coefficient of friction sufficient to grip the previous layer of wrap.

DESCRIPTION OF THE DRAWINGS

These and other features, aspects and advantages of the present invention will become better understood with regard to the following description, appended claims, and accompanying drawings where:

DESCRIPTION

Overview

Figure 1:
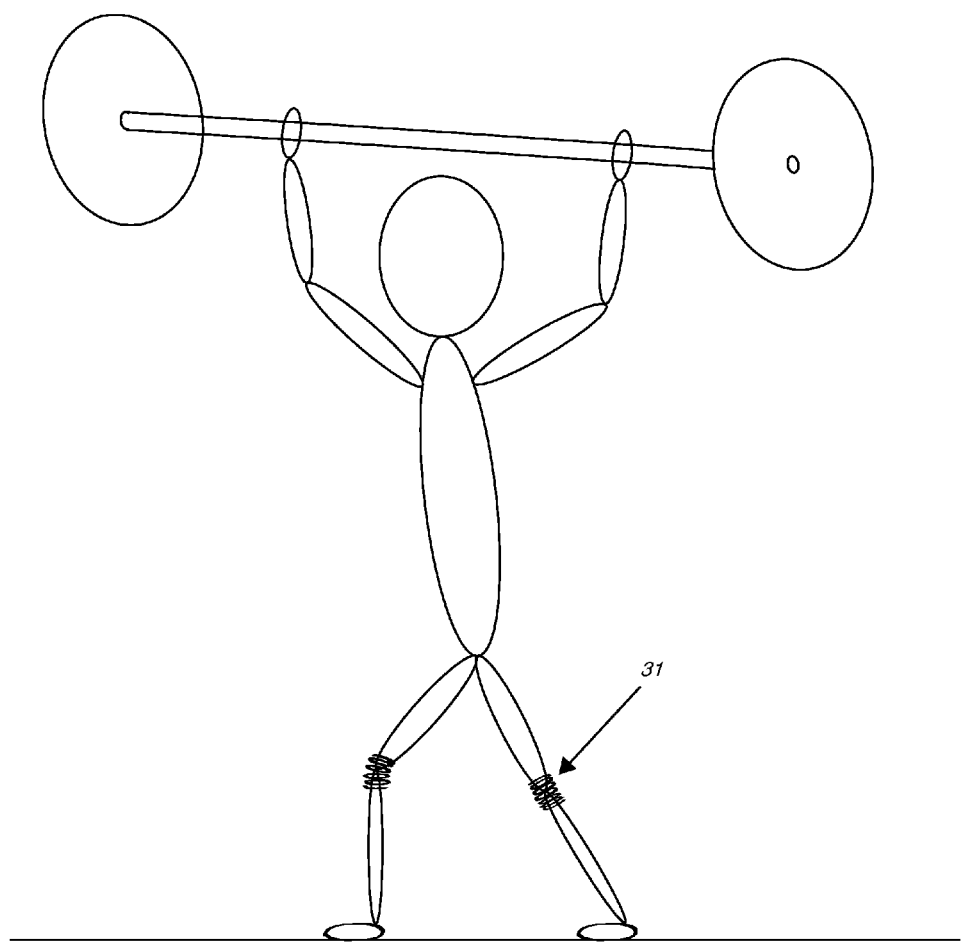
FIG. 1 shows a perspective illustration of a weightlifter engaging in a squatting exercise, showing an embodiment of gripper wraps wound around the knees.
Figure 2:
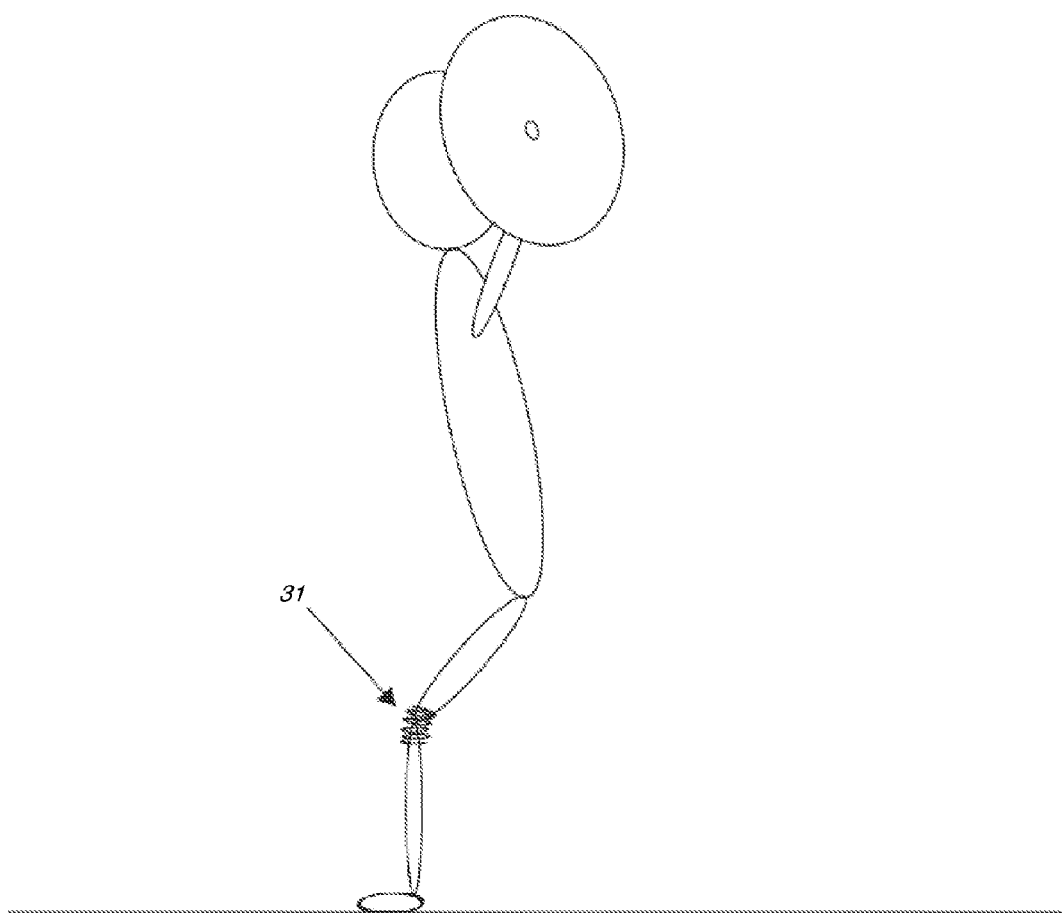
FIG. 2 shows a side view illustration of a weightlifter engaging in a squatting exercise, showing and embodiment of gripper wraps wound around the knees.
Figure 3:
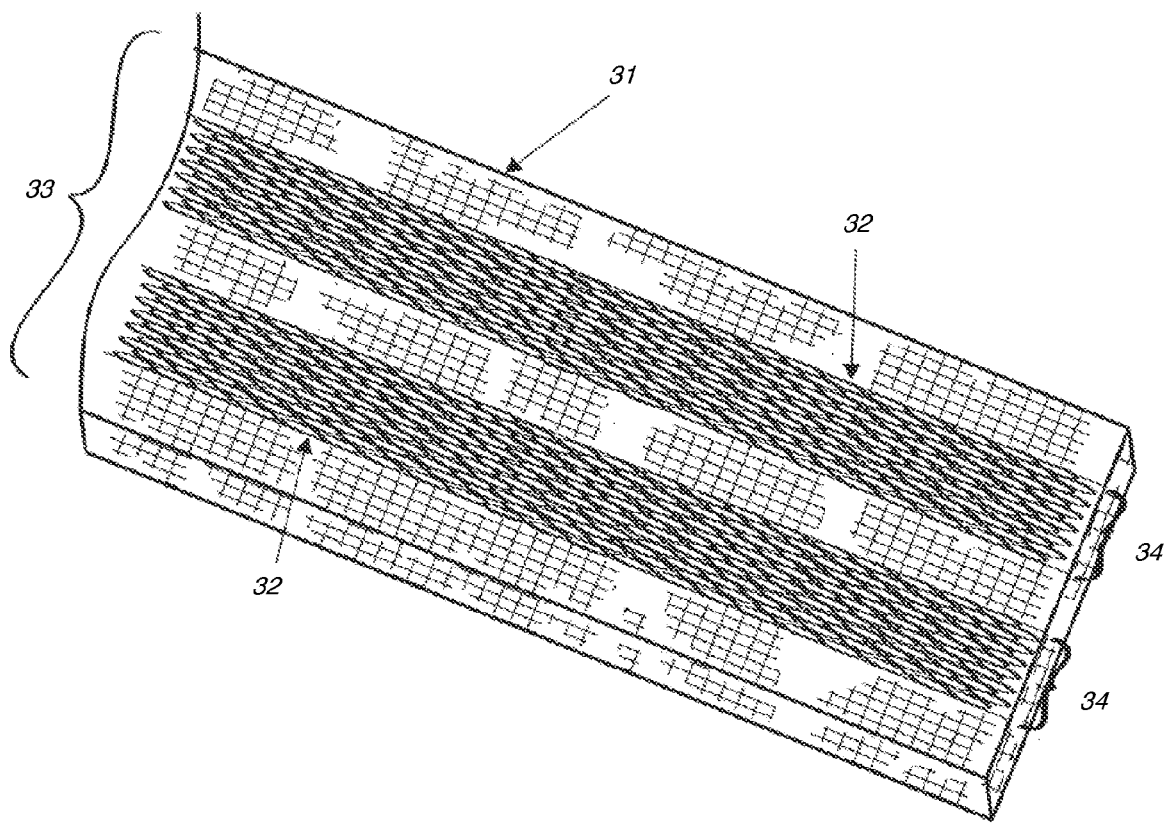
FIG. 3 shows a perspective view of an embodiment of the invention.
Figure 4:
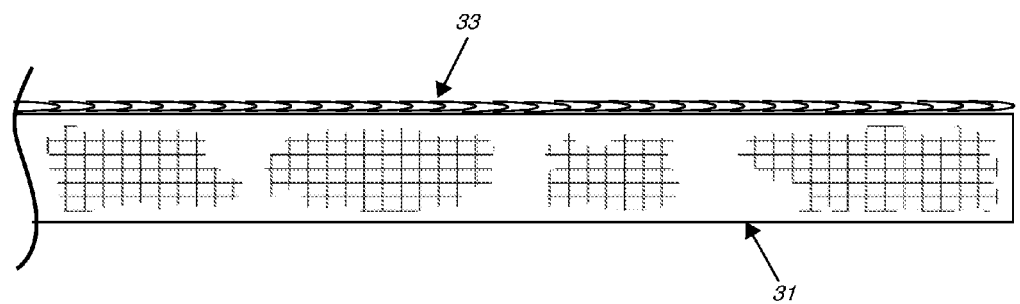
FIG. 4 shows a side view of the embodiment of FIG. 3.
Figure 5:
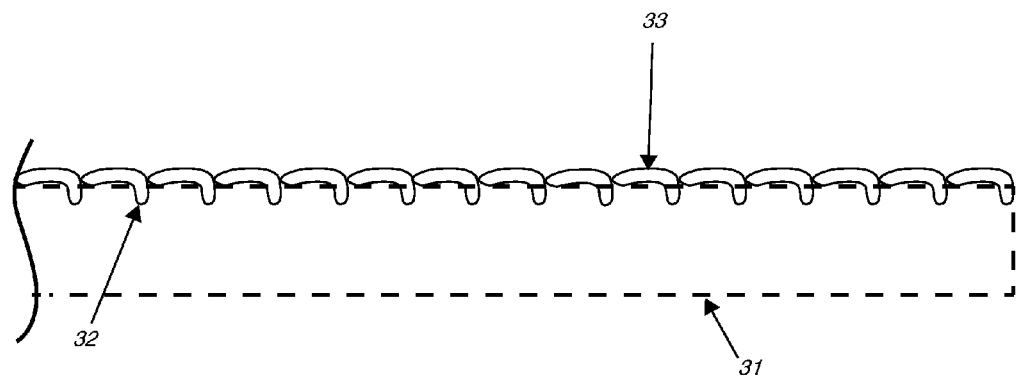
FIG. 5 shows a side sectional view of the embodiment of FIG. 3.
Figure 6:
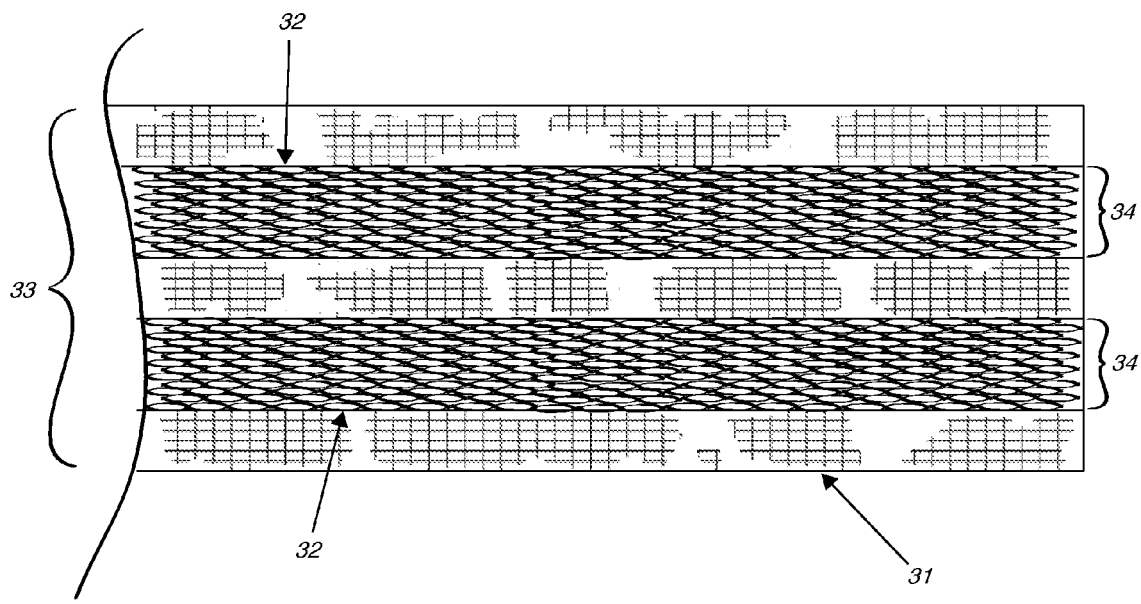
FIG. 6 shows a top view of the embodiment of FIG. 3.
Figure 7:
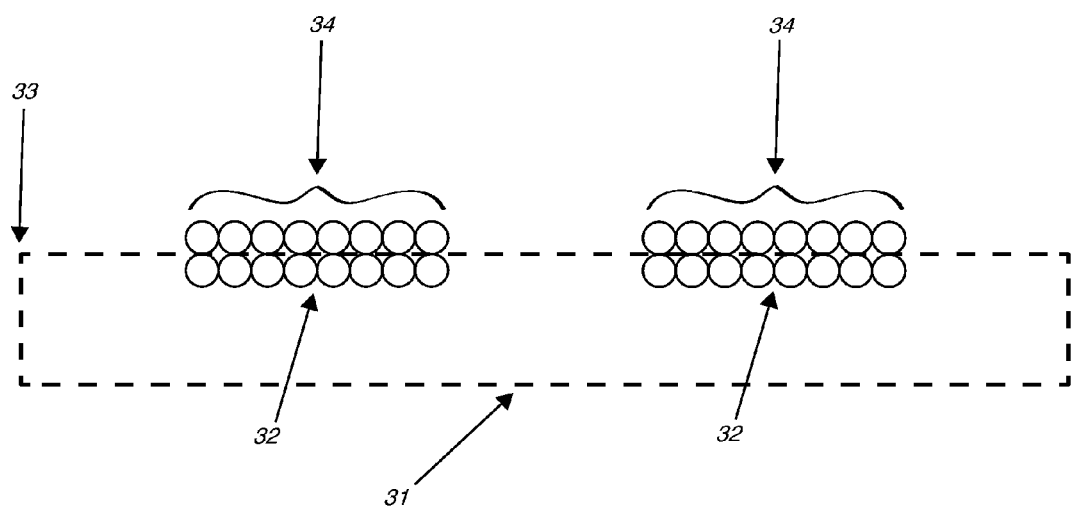
FIG. 7 shows a front sectional view of the embodiment of FIG. 3.

The gripper wraps of embodiments of the current invention integrate exposed rubber strands on at least one of the outer peripheral surface of said gripper wrap. The rubber strands secure the material of the proximate layers of wrap, thereby fixedly engaging the layers wrap in place relative to the previous layer of wrap. This holding or gripping action prevents the wrap from sliding and slipping on itself. The weightlifter no longer needs to spray sticky or apply chalk to the wrap material. The weightlifter no longer has to breathe toxic fumes from sticky spray or dust from chalk. Clothing is kept clean of chalk and sticky spray. This saves time, laundry expense and wear-and-tear to clothing, gym bags and other gear that touch the wraps. The athlete saves time by simply picking up the wraps, rolling the wraps on the joints, and enjoying the benefits of secure joint protection and increased performance.

The exposed rubber strands of the gripper wraps of embodiments of the invention provide a bulk of rubber material behind the joint. The bulk of rubber behind the joint provides a superior rebound effect (as opposed to weightlifting wraps without exposed rubber strands). The rubber is compressed behind the joint during joint flexion. The compressed rubber reacts against the surfaces surrounding the joint and rebounds the leg to a straight position with more kinetic energy return than weightlifting wraps without exposed rubber strands.

In embodiments of the current invention, exposed rubber strands of the gripper wraps are integrated into the woven wrap material in a manner to maximize the coefficient of friction between the proximate wound layer; to provide elastic rebound; and to allow greater circulation due to the stretching of the rubber strands. Rubber wrap designs which are not exposed (including rubber strands include inside a wrap, as opposed to outside of the wrap) must arranged be in a straight line. These straight-line rubber strands squeeze when stretched around the knee. Conversely, in embodiments of the current invention, a grouping of rubber strands in the exposed rubber strands of gripper wraps can be relatively loosely. Accordingly, such a configuration does not increase the modulus and squeezing sensation of the wrap when tightly wound.

The maximum length a weightlifting wrap can be pulled is usually determined by the weave of the cloth yarn. In embodiments of the current invention, the looped or braided construction/arrangement of the exposed rubber strands is still relatively loose as the wraps reach maximum pulled length. This results in less squeezing on body tissues as well as providing more rubber-bulk behind the knees than stretched-out rubber or wadded cloth yarn.

Occasionally when wrapping, the weightlifter or the weightlifter's handler loses hand grip on the wrap. When slipping begins to occur, the weightlifting gripper wraps of embodiments of the current invention do not uncoil, but merely lose tightness on only one revolution of wrap. The previously wrapper layers of the weightlifting gripping wraps remain as tight as when they were first pulled tightly on the knees. The weightlifter or the weightlifter's handler simply starts wrapping where they left off. If the weightlifting gripper wrap does become untucked, the wrap does not uncoil very far, usually less than two revolutions.

The gripper wraps of embodiments of the current invention reduce the "jittery" motion around the joints. As point load pressures are exerted on the joint, the weightlifting wraps of embodiments of the current invention stay tightly wrapped. Accordingly, the weightlifter conserves mental and physical energy which increases performance during competitions and workouts. Longevity and health are promoted due to the increased stability.

Specific Embodiments and Examples

An example of an embodiment of the invention is set forth in Drawing FIGS. 1-7, and is further described as the preferred design and best mode of carrying out the invention. According to the embodiment, the gripper wraps further comprise: weightlifting wraps 31 constructed of a pliable and stretchable material; the weightlifting wraps 31 having exposed rubbers strands 32 on at least one outer surface 33 of the weightlifting wraps; the exposed rubber strands 32 arranged in an offset lattice configuration, wherein the exposed rubber strands 32 have a coefficient of friction sufficient to grip the previous layer of wrap.

The weightlifting wraps 31 of the preferred embodiment are constructed of stretchable cloth material. The weightlifting wraps 31 may be of varying length and width, however in the preferred embodiment, the weightlifting wraps 31 are two meters (2 m) long and three inches (3") wide. The weightlifting wraps are constructed of 100% polyester. The weightlifting wraps in the preferred embodiment of this example have an approximate thickness of one-eighth of an inch (⅛").

The exposed rubber strands 32 are located on the outer surface 33 of the weightlifting wraps 31. The exposed rubber strands 32 are elongate pliable members, constructed of synthetic rubber. The exposed rubber strands 32 ingress and egress the outer surface of the weightlifting wraps 31 in an offset lattice configuration as shown in Drawing FIG. 3. For purposes of this invention, the offset lattice configuration involves including a small length of synthetic rubber interwoven through the outer surface 33 of the weightlifting wraps 31. An individual elongate pliable member of the exposed rubber strand 32 ingresses into the outer fabric of the weightlifting wraps 31 and extends a distance below the surface. The individual elongate pliable member of the exposed rubber strand 32 egresses around the proximate elongate pliable member of the exposed rubber strand 32, as shown in FIGS. 3-7. A plurality of small rubber loops are wound in this way, and longitudinally extend the length of the weightlifting wrap 31. Additional rows of rubber loops are added adjacent to the previous row, and the point at which the exposed rubber strand 32 enters the fabric is offset, in respect to the adjacent row, as shown and illustrated in Drawing FIGS. 3-7. A number of rows of exposed rubber strands 32 adjacent to each other form a band 34 of exposed rubber strands. The current embodiment includes two bands 34, wherein each band 34 is comprised of fourteen (14) rows of exposed rubber strands, wherein each row extend longitudinally the length of the weightlifting wraps 31, as shown in Drawing FIGS. 3-7.

In the current embodiment, the weightlifting wraps 31 are wrapped in such a manner that the exposed rubber strands 32 face away from the skin. The weightlifting wraps 31 are wrapped tightly around the joint, with the exposed rubber strands making contact with the next layer. During application and flexion of the joint, the weightlifting wraps 31 may stretch. The offset lattice configuration of the exposed rubber strands 32 allows the stretching to take place, without restricting blood flow. The compression of the exposed rubber strands 32 allows rebound on joint extension.

Alternatives

Figure 8:
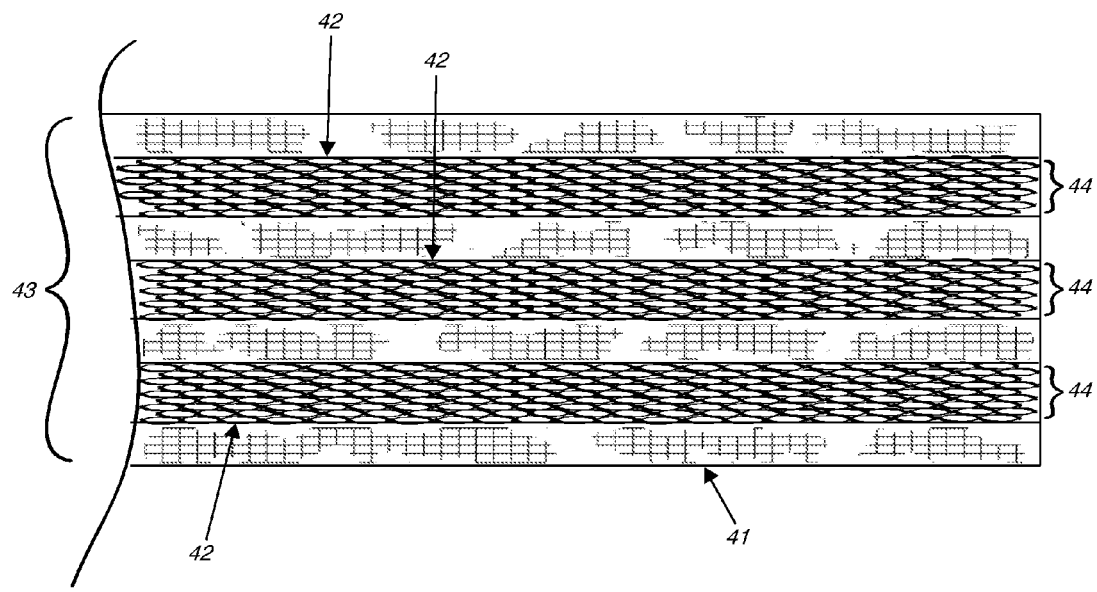
FIG. 8 shows a top view of an alternate embodiment of the invention, wherein the gripper wraps have three bands of exposed rubber strands traversing longitudinally across the outer surface.

Differing configurations and designs are contemplated by the current invention. For example, in an alternate embodiment of the invention, the structures and relational similarities of the preferred embodiment are employed. However, in the embodiment, the weightlifting wraps 41, have three bands 44 of exposed rubber strands 42 traversing longitudinally across the outer surface 43 distance of the weightlifting wraps 41. An example of this embodiment is illustrated in Drawing FIG. 8.

Figure 9:
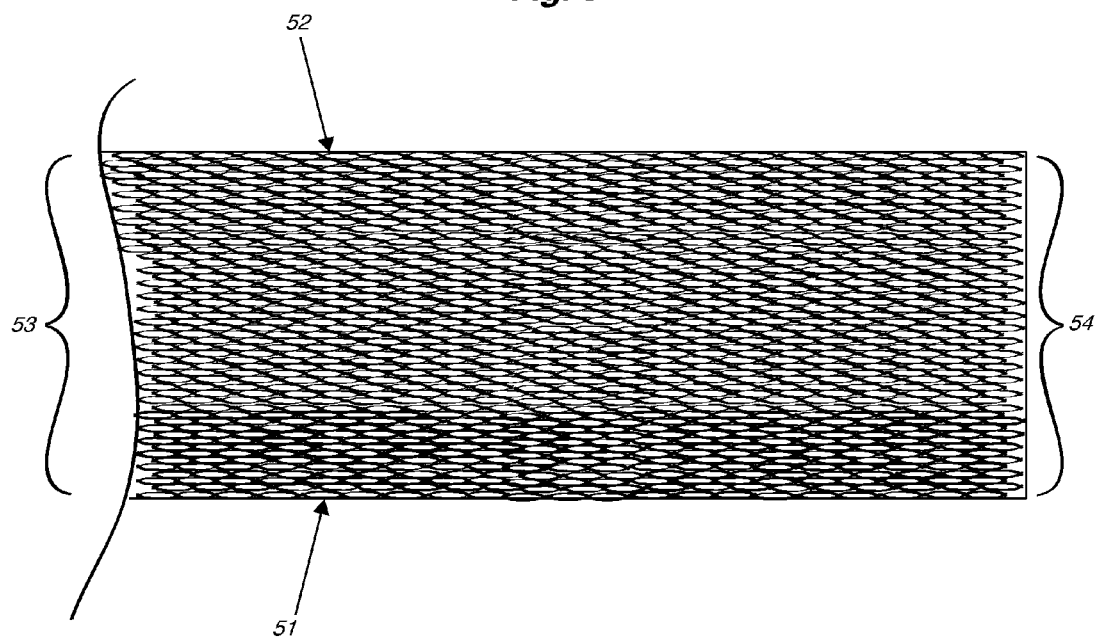
FIG. 9 shows a top view of an alternate embodiment of the invention, wherein the gripper wraps have one band of exposed rubber strands which covers the entire outer surface and traverses longitudinally the distance of the outer surface.

In another embodiment, the structures and relational similarities of the preferred embodiment are employed. However, the weightlifting wraps 51, have one band 54 of exposed rubber strands 52 which covers the entire outer surface 53, and traverses longitudinally the distance of the weightlifting wraps 51. An example of this embodiment is illustrated in Drawing FIG. 9.

Figure 10:
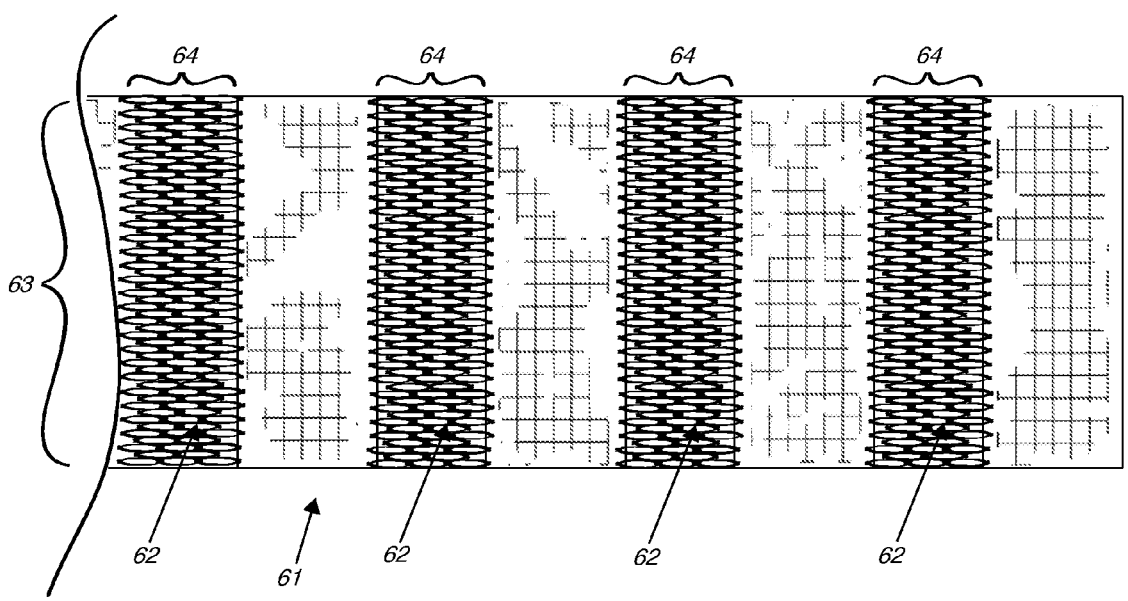
FIG. 10 shows a top view of an alternate embodiment of the invention, wherein the gripper wraps have a plurality of bands of exposed rubber strands which extend longitudinally perpendicular across the outer surface.

In another embodiment, the structures and relational similarities of the preferred embodiment are employed. The weightlifting wraps 61, have a plurality of bands 64 of exposed rubber strands 62 which extend longitudinally perpendicular across the outer surface 63, as illustrated in Drawing FIG. 10. The plurality of bands 64 extend the distance of the weightlifting wraps 61. An example of this embodiment is illustrated in Drawing FIG. 9.

In other embodiments, the materials used in the preferred embodiment may differ. For example, the weightlifting wraps 31 of the preferred embodiment may be constructed from: polyester; elastic; cotton fiber, medical crepe; or combinations and equivalents thereof. The loft of yarn used may vary. In the preferred embodiment, the loft of yarn was chosen such that the weightlifting wraps were tightly woven and presented a softer surface to the underlying tissue. Alternatively, a loft of yarn may be used that presents a harder surface to the underlying tissue.

In other embodiments, the configuration, placement, length, width, and placement of bands 34 may differ according to alternate embodiments. For example, the exposed rubber strands 32 can be arranged so that they encompass differing patterns, and shapes, and encompass differing dimensional relationships. The width, length, and thickness of the weightlifting wraps 31 may also differ. In other embodiments, the exposed rubber strands may be interwoven through both outer sides of the weightlifting knee wraps in the configurations previously set forth. The exposed rubber strands 32 may also be constructed of a different material such exposed rubber strands 32 have a coefficient of friction great enough to grip the previous layer of wrap.

Use of embodiments of the current invention may applied in weightlifting exercises or in situations where it is desirable for an athlete or weightlifter to provide support and kinetic energy rebound to the joints. Examples of embodiments of the current invention as previously set forth were directed towards knee wraps, however it is also contemplated by embodiments of the current invention for use of the wraps on other parts of the body. For example, the weightlifting wraps may be placed on the: ankles, legs, knees, waist, torso, elbows, or wrists.

Differing combinations and permutations of the embodiments set forth are contemplated by the current invention. Additionally, all functional equivalents of materials used and means of attachment of elements are contemplated by the current invention. Therefore, the spirit and scope of the appended claims should not be limited to the descriptions of the preferred versions and alternate embodiments set forth herein.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

What is claimed is:

1. Gripper wraps comprising: weightlifting wraps constructed of a stretchable material; said weightlifting wraps having a plurality of exposed rubber strands on at least an outer surface of said weightlifting wraps; said exposed rubber strands ingress and egress said outer surface of said weightlifting wraps and are arranged in an offset lattice configuration, and wherein said exposed rubber strands have a coefficient of friction sufficient to grip the previous layer of said weightlifting wraps.

2. The gripper wraps of claim 1, wherein the weightlifting wraps are constructed of 100% polyester material.

3. The gripper wraps of claim 1, wherein the weightlifting wraps are either of polyester; elastic; cotton fiber, medical crepe; or combinations thereof.

4. The gripper wraps of claim 1, wherein the exposed rubber strands are elongate pliable members constructed of synthetic rubber.

5. Gripper wraps comprising: weightlifting wraps constructed of a stretchable material; said weightlifting wraps having a plurality of exposed rubber strands on at least an outer surface of said weightlifting wraps; wherein a plurality of rows of exposed rubber strands ingress and egress said outer surface of said weightlifting wraps in an offset lattice configuration such that they form a band; and wherein said exposed rubber strands are elongate pliable members constructed of synthetic rubber and have a coefficient of friction sufficient to grip the previous layer of said weightlifting wraps.

6. The gripper wraps of claim 5, wherein a band is comprised of 14 rows of exposed rubber strands, wherein each row of said exposed rubber bands extends longitudinally the length of said weightlifting wraps.

7. The gripper wraps of claim 6, wherein the weightlifting wraps comprise two of said bands.

8. The gripper wraps of claim 5, wherein the weightlifting wraps comprise three or more of said bands traversing longitudinally across the outer surface distance of said weightlifting wraps.

9. The gripper wraps of claim 5, wherein the weightlifting wraps comprise one of said bands which covers an outer surface of said weightlifting wraps, and traverses longitudinally the distance of said weightlifting wraps.

10. The gripper wraps of claim 5, wherein the weightlifting wraps comprise a plurality of bands which extend longitudinally perpendicular across an outer surface of said weightlifting wraps.

11. The gripper wraps of claim 5, wherein the exposed rubber strands extend across both outer surfaces of said weightlifting wraps.

12. Gripper wraps comprising: weightlifting wraps constructed of a stretchable and pliable material; said weightlifting wraps having a plurality of exposed rubbers strands on at least an outer surface of said weightlifting wraps; said exposed rubber strands arranged such that an individual elongate pliable member of said exposed rubber strand ingresses into the outer fabric of said weightlifting wraps and extends a distance below the outer surface of said weightlifting wraps, said individual elongate pliable member of said exposed rubber strand egresses around the proximate elongate pliable member of said exposed rubber strand, wherein the point at which said exposed rubber strand ingresses said weightlifting wraps is offset, in respect to the adjacent row of said exposed rubber strands; wherein said exposed rubber strands have a coefficient of friction sufficient to grip the previous layer of said weightlifting wraps.

13. The gripper wraps of claim 12, wherein rows of said exposed rubber strands extend longitudinally the distance of said weightlifting wraps, such that they form a band.

14. The gripper wraps of claim 12, wherein the weightlifting wraps comprise a plurality of bands.

15. The gripper wraps of claim 12, wherein said exposed rubber strands are located on both outer surfaces of said weightlifting wraps.

\* \* \* \* \*